US005593962A

United States Patent [19]
Arvinte et al.

[11] Patent Number: 5,593,962
[45] Date of Patent: Jan. 14, 1997

[54] FIBRILLATED CALCITONIN PHARMACEUTICAL COMPOSITIONS

[75] Inventors: Tudor Arvinte; Amelia Cudd, both of Billingshurst; Judith Phillips, Sevenoaks, all of England

[73] Assignee: Ciba-Geigy Corporation, Tarrytown, N.Y.

[21] Appl. No.: 102,117

[22] Filed: Aug. 4, 1993

Related U.S. Application Data

[63] Continuation of Ser. No. 866,672, Apr. 10, 1992, abandoned.

[30] Foreign Application Priority Data

Apr. 23, 1991 [GB] United Kingdom .................. 9108634

[51] Int. Cl.$^6$ .......................... A61K 38/00; A61K 38/02; A61K 38/30; C07K 5/00
[52] U.S. Cl. ............................... 514/12; 514/11; 530/300; 530/307; 530/324
[58] Field of Search ........................ 514/12, 11; 530/307, 530/300, 324

[56] References Cited

U.S. PATENT DOCUMENTS 4,690,952  9/1987  Kagatani et al. ........................ 514/808

FOREIGN PATENT DOCUMENTS 277462  12/1986  European Pat. Off. .

OTHER PUBLICATIONS

Arvinte, et al "Comparative Study of Human and Salmon Calcitonin Secondary Structure in Solutions With Low Dielectric Constants" J. Biol. Chem. 268(9):6408–6414 (1993).
Arvinte, et al. "The Structure and Mechanism of Formation of Human Calcitonin Fibrils" J. Biol. Chem 268(9):6414–6422 (1993).
Sieber, et al. "Menschliches Calcitonin. Die Synthese Von Calcitonin M$^2$" Helvetica Chimica Acta 53:2135–2150(1970)–includes English Summary.
European Search Report dated 14 Jul. 1993.
Sieber P, et al. "Menschliches Calcitonin VT$^1$). Die Synthese von Calcitonin M$^2$)" Helvetica Chimica Acta. 53(8)2135–2150 (1970) (Abstract).
Levy, et al. "Formation of Neutralizing Antibodies During Intranasal Synthetic Salmon Calcitonin Treatment of Pagets Disease", J. Clin. Endocrinol. Metab. 67:541–545 (1988).
Grauer, et al. "In Vitro Detection of Neutralizing Antibodies After Treatment of Pagets Disease of Bone With Nasal Salmon Calcitonin" J. Bone Min Res. 5(4):387–391 (1990).
Dietrich, et al. "Synthetic Human Calcitonin: Analysis of Antibodies Obtained from Various Animal Species and Determination of Immunoreactive Hormone in Human Sera" Acta Endocrinol. 80:465–485 (1975).
Dietrich, et al "Formation of Antibodies to Synthetic Human Calcitonin During Treatment of Pagets Disease" Acta Endocrinol. 92:468–476 (1979).

Moran, et al. "Calcitonin and Calcium Inophores: Cyclic AMP responses in cells of a human lymphoid line" Proc. Natl. Acad. Sci 75(8)3984–8 (1978).
Aloia, et al. "Treatment of Osteoporosis With Calcitonin, With and Without Growth Hormone" Metabolism 34(2):124–129 (1985).
Gruber, et al "Long Term Calcitonin Therapy in Postmenopausal Osteoporosis" Metabolism 33(4):295–303 (1984).
Rojanasathit, et al. "Pagets Bone Disease: Response To Human Calcitonin In Patients Resistant To Salmon Calcitonin" Lancet 2:1412–1415 (1974).
Singer et al, "An Evaluation of Antibodies and Clinical Resistance to Salmon Calcitonin" J. Clin Invest 51(3):2331–2338 (1972).
Herbert, et al. "Coated Charcoal Immunoassay of Insulin" J Clin Endocrinol Metals 25:1375–1384 (1965).
Roos et al. "Evaluation of the in Vivo and in Vitro Calcium Regulating Actions of Noncalcitonin Peptides Produced via Calcitonin Gene Expression" Endocrinology 118(1):46–51 (1986).
Woodhouse, et al "Development and Significance of Antibodies to Salmon Calcitonin in Patients With Pagets Disease on Long Term Treatment" Br Med J 2:927–929 (1977).
Raue, et al. "Action of Calcitonin Gene Related Peptide at the Calcitonin Receptor of the T47D Cell Line" Horm Metabol Res 19:563–4 (1987).
Nagant, et al "New Modes of Administration of Salmon Calcitonin in Pagets Disease" Clin Orthop Rel Res 217:56–71 (1987).
Findlay, et al "Calcitonin and 1,25–dihydroxyvitamin $D_3$ receptors in Human Breast Cancer Cell Lines" Cancer Res 40:4764–4767 (1980).
Pontiroli, et al "Intranasal Calcitonin and Plasma Calcium Concentrations in Normal Subjects" Br Med J 290:1390–1391 (1985).
Singer, et al "Salmon Calcitonin Therapy for Pagets Disease of bone" Arthritis Rheun 23:1148–1153(1980).
Altman, et al "Synthetic Human Calcitonin in Refractory Paget's Disease of Bone" Arch Intern Med 147:1305–1308 (1987).
Wohlwend, et al. "Calcitonin and Calcitonin Gene–Related Peptide Interact with the Same Receptor in Cultured LLC–PK$_1$ Kidney Cells" Biochem Biophys Res Commun 131(2):537–542 (1985).
Lamp, et al "Calcitonin Induction of a Persistant Activated State of Adenylate Cyclase in Human Breast Cancer Cells" (T47D) J. Biol Chem 256(23):12269–74 (1981).
DeRose, et al "Response on Pagets Disease to Porcine and Salmon Calcitonin" Am J Med 56:858–866 (1974).

(List continued on next page.)

Primary Examiner—Christina Y. Chan
Assistant Examiner—A. M. Davenport
Attorney, Agent, or Firm—Irving M. Fishman; Karen G. Kaiser; Marla J. Mathias

[57] ABSTRACT

The invention provides fibrillated calcitonin for use in treating calcium deficiency diseases.

13 Claims, 4 Drawing Sheets

OTHER PUBLICATIONS

Haddad, et al. "Calcitonin Resistance Clinical and Immunologic Studies in Subjects With Pagets Disease of Bone Treated With Porcine and Salmon Calcitonin" J Clin Invest 51:3133–40 (1972).

Armbruster, F. P. et al "C–AMP Protein Bindungs Assay: Proteinabhangigkeit der cAMP–Bindung" Aerztl Lab 32:115–120 (1986).

Diem, et al. Documenta Geigy Wissenschaftliche Tabellen, ed 7 p. 146 (1968).

Mazzuoli, et al. "Effects of Salmon Calcitonin in Postmenopausal Osteoporosis: A Controlled Double–Blind Clinical Study" Calcif Tissue Int 38:3–8 (1986).

Buclin, et al. "The Effect of Rectal and Nasal Administration of Salmon Calcitonin in Normal Subjects" Calcif Tissue Int 41:252–258 (1987).

Kurose, et al "Intranasal Absorption of Salmon Calcitonin" Calcif Tissue Int 41:249–251 (1987).

Reginster, et al "Salmon Calcitonin Nasal Spray in Pagets Disease of Bone: Primary Results in Five Patients" Calcif Tissue Int 37:577–580 (1985).

LoCascio, et al "Response of Paget's Disease to Human Calcitonin in Patients Resistant to Porcine Calcitonin" J Endrocrinol Invest 7:85–88 (1984).

Nagant de Deuxchaisnes "Effect of a Nasal Spray of Salmon Calcitonin in Normal Subjects and Patients with Pagets Disease" Calatonin 329–343 (1984).

Singer, et al. "Pagets Bone Disease: Etiologic and Therapeutic Aspects" Bone and Mineral Research vol. 2:394 (1983).

FIBRILLATED CALCITONIN PHARMACEUTICAL COMPOSITIONS

CROSS-REFERENCE TO RELATED APPLICATION

This is a continuation of Ser. No. 07866,672, filed Apr. 10, 1992, now abandoned.

BACKGROUND OF THE INVENTION

The present invention relates to pharmaceutical compositions comprising calcitonin.

Calcitonin is a 32 amino acid polypeptide hormone secreted by the parafollicular cells of the thyroid gland in mammals and by the ultimobrachial gland of birds and fish. It is a potent drug for the treatment of Paget's disease, some aspects of hypercalcaemia, and for postmenopausal osteoporosis. Calcitonins of different origins, mainly salmon, pig, eel, and human are currently used therapeutically.

Human calcitonin, although considered less potent and thus required at higher concentrations or doses than salmon calcitonin, has the advantage of not generating neutralizing antibodies after prolonged administration as the salmon calcitonin does (Grauer et at. 1990, J. Bone Min. Res. 5,387–391, Levy et at. 1988, J. Clin. Endocrinol. Metab. 67,541–545 and the references therein).

In physiological saline solutions or buffers, human calcitonin is not stable, it precipitates and forms gels which consist of calcitonin fibrils. Since fibrillated calcitonin does not redissolve in physiologically compatible solutions, the calcitonin fibrils per se have not been considered for therapeutic use. Due to the fibril formation phenomenon, which was perceived to be undesirable, various steps have been adopted to avoid the problem. In particular, the injectable dosage form of human calcitonin is made up only as and when required by mixing hCT powder and the aqueous solution immediately prior to injection. This procedure is not required for salmon calcitonin which is provided in stable solution.

We have now found, surprisingly that calcitonin fibrils per se are biologically active and give a longer-time dose response than calcitonin in solution.

BRIEF DESCRIPTION OF THE DRAWINGS

For a better understanding of the invention, reference is had to the following description taken in connection with the accompanying drawings, in which.

DESCRIPTION OF THE PREFERRED EMBODIMENTS

Figure 1A:
FIG. 1a is an electron micrograph of negatively stained sonicated hCT fibrils prepared in accordance with the invention.

Accordingly the present invention provides fibrillated calcitonin for use in treating calcium deficiency diseases.

The calcitonin is preferably human calcitonin (hCT) which may be synthetic or it may be produced by recombinant DNA technology, it may be salmon, eel or porcine calcitonin.

The term "human calcitonin" is used in a broad sense in the context of this description and is intended to comprise not only natural human calcitonin as described in Helv. Chim. Acta, Vol 53, loc. cit., which can also be obtained synthetically, but also pharmaceutically acceptable derivatives and analogues thereof, e.g. those in which one or more of the amino acid groups occurring in the natural compounds are replaced or the N- or C-terminal group has been structually modified.

Human calcitonin can exist in the free form or in the form of a pharmaceutically acceptable acid addition salt. Such salts are known and their activity and compatibility are comparable to those of the free forms. Typical suitable acid addition salts are the hydrochlorides or acetates.

Calcitonin may be fibrillated by adding water or an aqueous solution to calcitonin powder and then stirring to dissolve. Suitable aqueous solutions include dilute solutions of NaCl, e.g. 0.9% NaCl; weak acids, e.g. 0.001% to 0.5% acetic acid; and buffers, e.g. phosphate saline buffer at pH 7.4 or other biologically compatible buffers. The solution may then be incubated at a temperature from 2°–50° C., preferably at room temperature for the fibrillation reaction to be completed, i.e. when there are no more changes in the samples turbidity. The incubation time is dependent on the aqueous medium, the temperature and on the concentration of calcitonin. The concentration of calcitonin may be from 1 to 200 mg/ml, preferably from 5 to 100 mg/ml. Solutions of higher concentration fibrillate faster and fibrillation occurs faster at higher temperatures. It has been found that, for the fibrillation process to be completed, an incubation period of 1 hour is needed for a 200 mg/ml hCT solution in water.

The fibrillated calcitonin may be used in the gel form. In this form it acts as a depot and can be administered intramuscularly, intra-nasally, sub-cutaneously, or orally, e.g. intra-colonically. The fibrillated gels can be squeezed through injection needles. In this case it is preferred to place the calcitonin solution in a syringe, sterilise it and then allow it to fibrillate in the syringe, after which it is ready for use. The solution is preferably placed in the syringe at a low temperature to delay fibrillation. When in the syringe the temperature can be raised.

If desired the calcitonin fibrils may be fragmented or disrupted by any suitable method such as in a blender or homogeniser or preferably by ultrasound treatment (sonication). Electron microscopy analysis of a sonicated hCT fibril suspension shows that it consists of small rods of about 15 nm diameter and 26 to 130 nm in length.

In order to fragment or disrupt the fibrils, a further volume of water or aqueous solution is added to the fibrils and the resulting mass is subjected, preferably, to sonication using, for example, a tip sonicator until the fibrils are completely disrupted and no further changes in the sample's turbidity occurs with further sonication. During the sonication, the temperature is preferably maintained below 37° C. Constant temperature conditions are preferred, e.g. by surrounding the sample with ice. The sonication is also preferably carried out under an inert gas atmosphere such as nitrogen or argon.

The aqueous solution added to the gel may be one such as is used in forming the original solution.

The fragmentation is preferably carded out within 24 hours of the end of the incubation.

The resulting product is a dispersion of fragmented fibrils in the water or aqueous solution and this dispersion forms a further aspect of the present invention.

When used as a gel, the concentration of calcitonin may be from 1 to 200 mg/ml, preferably from 5 to 100 mg/ml. When used as a dispersion of fragmented fibrils the concentration of calcitonin may be up to 50 mg/ml.

Preferred ranges for fragmented hCT fibril suspensions are from 3 to 10 mg/ml for nasal or oral solutions and from 0.5 to 3 mg/ml for injectable solutions.

The compositions of the invention have a prolonged hypocalcemic effect such that in calcitonin therapy the number of injections required, or doses to be taken can be reduced, compared to those needed when conventional calcitonin solutions are used.

The compositions of the invention may also contain viscosity-increasing swelling agents and/or sugars and/or other pharmaceutically acceptable additives. As viscosity-increasing swelling agents there may be used hydrophilic partially etherified cellulose derivatives, hydrophilic polyacrylates, polymethacrylates, polyethylene glycols, polyvinyl alcohols or mixtures thereof. Suitable compounds include methyl cellulose, hydroxypropylmethylcellulose, polyethylene glycol, dextran, which may have a molecular weight of 20,000 to 80,000, but preferably about 40,000, sugars such as sucrose, fructose, glucose, lactose, mannitol and trehalose, ethanol, serum albumin, lysozyme and preservatives such as benzalkonium chloride, benzethonium chloride and chlorhexidine diacetate.

The amount of additives used can vary and may depend on the intended use. For example for nasal or oral solutions, 0.5 to 10% by weight of additive may be used. In the case of injectable solutions, sugars, polyethylene glycols or dextran would be used as the additive, usually in amounts of 0.5 to 10% by weight.

The invention is illustrated in the following examples.

EXAMPLE 1

Figure 1B:
FIG. 1b is an electron micrograph of the original hCT fibrils.

200 µl of 0.001% acetic acid/water is added to 20 mg hCT powder and solubilisation is performed using a vortex mixer for 1–2 min. The resulting solution is allowed to fibrillate for 1 hour. Over the hard turbid gel of hCT-fibril are added 4 ml of 0.001% acetic acid; then ultrasonication is performed for 2 min. Electron micrographs of negatively stained sonicated hCT fibrils show the presence of rods as in FIG. 1a. The original hCT fibrils are shown in FIG. 1b. The rods of sonicated hCT fibrils were, on average, 15 nm in diameter and 26–130 nm long.

EXAMPLE 2

Following the procedure of Example 1, hCT fibrillated gels are formed from a solution of 20 mg hCT in 100 µl.01% acetic acid. 10ml water are then added and sonication performed as described in Example 1 with similar results.

EXAMPLE 3

Figure 2:
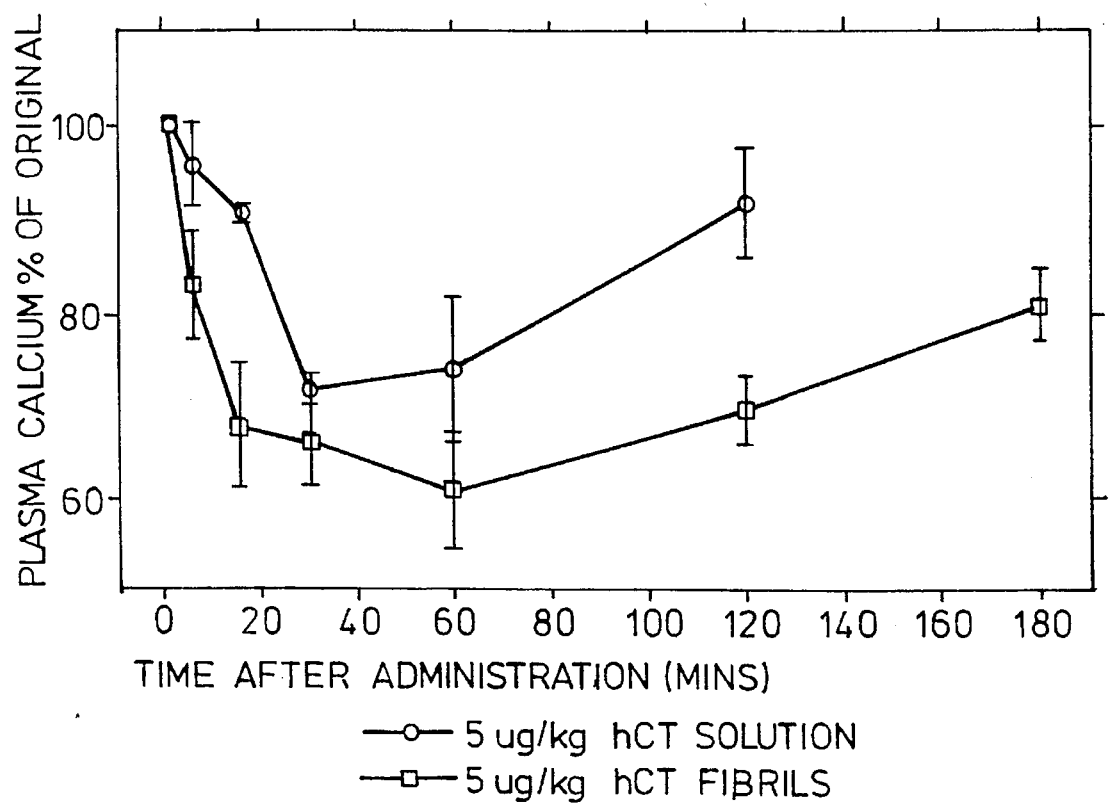
FIG. 2 is a graph depicting a comparison of hCT in solution and in sonicated fibrils on rat plasma calcium levels.

The product from Example 2 is diluted with 0.9% aqueous NaCl solution to give a solution having an hCT concentration of 5 µg/ml. This is injected intravenously into a hypocalcaemic rat model and compared with a similar injection of a solution of hCT made up in the conventional manner by dissolving hCT powder. The dosage in each case is 5 µg/kg body weight. The results are shown in FIG. 2. The solution of Example 2 is biologically active and has a longer time dose response than the conventional solution.

Figure 3:
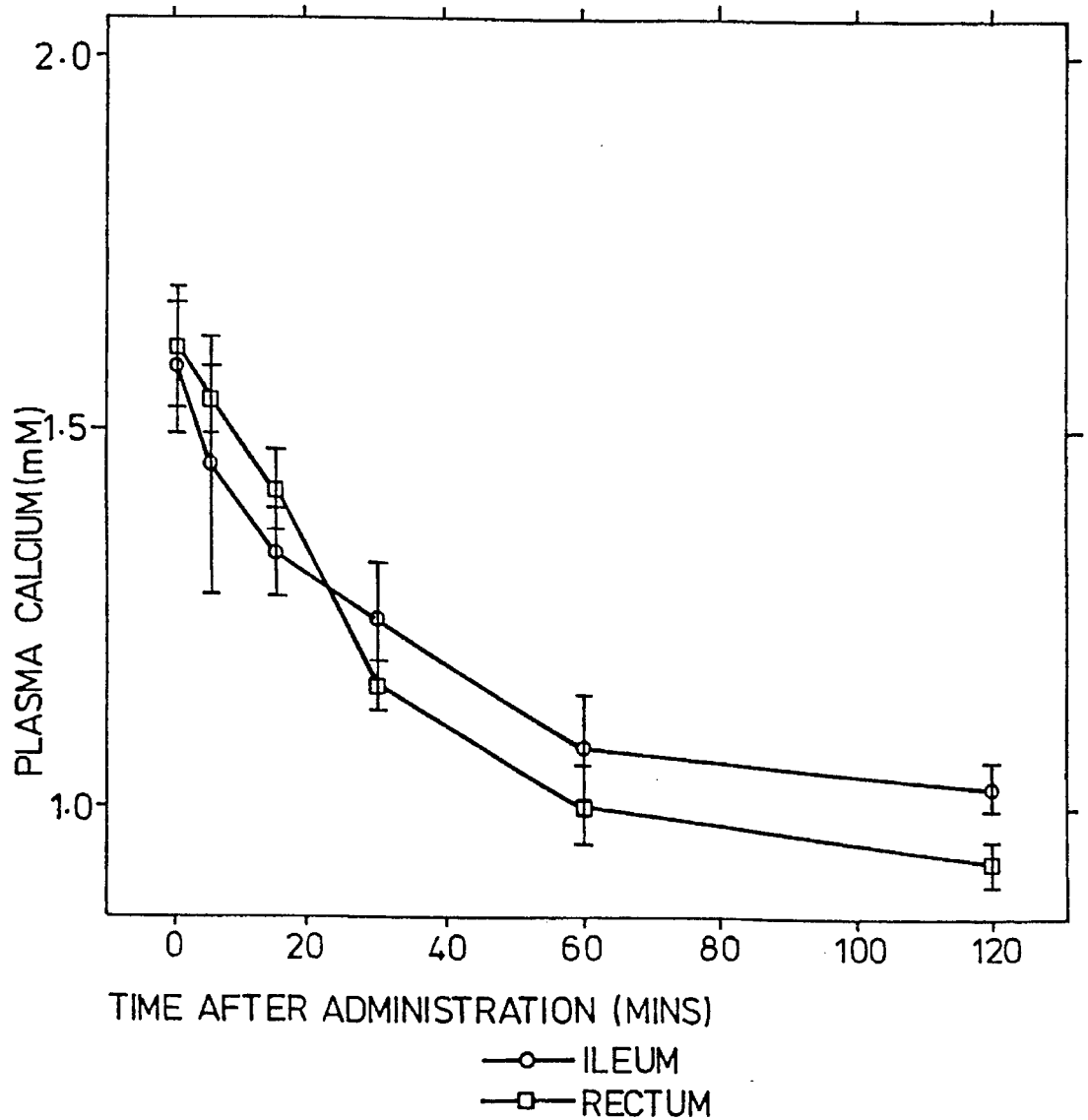
FIG. 3 is a graph depicting the effect of hCT fibrils in the ileum and rectum.

EXAMPLE 4 hCT fibrillated gels are formed by placing aqueous hCT solutions: (50 mg/ml hCT in 0.1% acetic acid or in 0.9% NaCl) in syringes and allowing the hCT to fibrillate in the syringes overnight. The sub-cutaneous (s.c.) intra-nasal (i.n.) intra-rectum (i.r.), intra-ileum (i.i.) or intra-colonical (i.c.) injection of hCT fibrillated gel can be done easily since the hardened fibrillated hCT gels can be squeezed through injection needles. FIG. 3 shows that in the hypocalcaemic rat model i.r., and i.i. injected hCT fibrillated-gel have a strong and prolonged biological effect. Fibrils formed in 0.9% NaCl were used for s.c. and i.n. experiments and fibrils formed in 0.1% acetic acid were used for the i.r., i.i. and i.c. experiments.

In the in vivo experiments in Examples 3 and 4 the following hypocalcaemic rat model is used:-Female Wistar rats 80–100g body weight are fed a normal diet. hCT is administered as mentioned to animals anaesthetised with Hypnorm then sodium pentabarbitone i.m. Blood samples (250 µl) are taken from a cannulated carotid artery at each time point. Change in calcium level after the administration of hCT formulations is measured by a colorimetric method using a Ca measuring kit (Sigma Chem. Co.). For each time point three to five animals are used.

We claim:

1. A method of treating calcium deficiency diseases which comprises administering a pharmaceutical composition comprising fibrillated calcitonin.

2. A method according to claim 1 in which the calcitonin is human, salmon, eel or porcine calcitonin.

3. A method according to claim 1 wherein the fibrillated calcitonin comprises fragmented fibrils of calcitonin.

4. A method according to claim 3 in which the fragmented fibrils are in the form of rods having an average diameter of about 15 nm and a length of 26 to 130 nm.

5. A method according to claim 1 in which the fibrillated calcitonin comprises calcitonin and water and optionally NaCl, a weak acid or a buffer.

6. A method according to claim 1 in which the pharmaceutical composition further comprises at least one additive selected from the group consisting of a viscosity-increasing gelling agent, and a sugar.

7. A process for preparing fibrillated calcitonin which comprises dissolving calcitonin in water or water and an additive selected from the group consisting of NaCl, a weak acid, a buffer, a viscosity-increasing gelling agent, and a sugar, and allowing fibrillation to occur.

8. A process as claimed in claim 7 which comprises the further steps of adding a further volume of water or water and an additive selected from the group consisting of NaCl, a weak acid, a buffer, a viscosity-increasing gelling agent, and a sugar, and fragmenting the fibrils.

9. A process as claimed in claim 8 in which the fibrils are fragmented by means of a blender, homogeniser or by sonication.

10. A process as claimed in claim 8 in which the step of fragmenting the fibrils is carried out at a temperature below 37° C.

11. A process as claimed in claim 8 in which the step of fragmenting the fibrils is carried out under an inert gas atmosphere.

12. A process as claimed in claim 7 in which the fibrillation is carried out in a syringe which is used to administer the calcitonin.

13. A dispersion of fragmented calcitonin fibrils in water or water and an additive selected from the group consisting of NaCl, a weak acid, a buffer, a viscosity-increasing gelling agent, and a sugar.

* * * * *